United States Patent [19]
Nielsen et al.

[11] Patent Number: 5,782,793
[45] Date of Patent: Jul. 21, 1998

[54] TAMPON APPLICATOR HAVING A SEMI-SPHERICALLY SHAPED PLEATED TIP

[75] Inventors: Steven James Nielsen, Greenville; Tammy Jo Rentmeester, Appleton; Allan James Krueger, Winneconne; Jeffrey Michael Weyenberg, Appleton, all of Wis.

[73] Assignee: Kimberly-Clark Worldwide, Inc., Neenah, Wis.

[21] Appl. No.: 802,458

[22] Filed: Feb. 18, 1997

Related U.S. Application Data

[63] Continuation of Ser. No. 422,117, Apr. 14, 1995, abandoned, which is a continuation-in-part of Ser. No. 294,230, Aug. 22, 1994, abandoned.

[51] Int. Cl.⁶ .................................................. A61F 13/20
[52] U.S. Cl. .................................................. 604/14; 604/15
[58] Field of Search ................................. 604/11–18, 904

[56] References Cited

U.S. PATENT DOCUMENTS

| | | |
|---|---|---|
| 2,413,480 | 12/1946 | Winter . |
| 2,639,646 | 5/1953 | Thompson et al. . |
| 2,922,422 | 1/1960 | Bletzinger . |
| 2,922,423 | 1/1960 | Rickard et al. . |
| 3,204,635 | 9/1965 | Voss et al. . |
| 3,358,354 | 12/1967 | Voss et al. . |
| 3,433,225 | 3/1969 | Voss . |
| 3,499,447 | 3/1970 | Mattes et al. . |
| 3,581,744 | 6/1971 | Voss . |
| 3,628,533 | 12/1971 | Loyer . |
| 3,674,026 | 7/1972 | Werner et al. . |
| 3,753,437 | 8/1973 | Hood et al. ............... 128/263 |
| 3,760,808 | 9/1973 | Bleuer . |
| 3,764,438 | 10/1973 | Voss et al. . |
| 4,211,225 | 7/1980 | Sibalis . |
| 4,318,404 | 3/1982 | Cunningham . |
| 4,351,339 | 9/1982 | Sneider . |
| 4,361,150 | 11/1982 | Voss . |
| 4,412,833 | 11/1983 | Wiegner et al. . |
| 4,413,986 | 11/1983 | Jacobs . |
| 4,573,963 | 3/1986 | Sheldon . |
| 4,610,659 | 9/1986 | Friese . |
| 4,650,459 | 3/1987 | Sheldon ............... 604/15 |
| 4,726,805 | 2/1988 | Sanders, III . |
| 4,857,044 | 8/1989 | Lennon ............... 604/904 |
| 4,960,417 | 10/1990 | Tarr, Jr. et al. . |
| 5,080,659 | 1/1992 | Nakanishi . |
| 5,087,239 | 2/1992 | Beastall et al. . |
| 5,153,971 | 10/1992 | Van Iten . |
| 5,158,535 | 10/1992 | Paul et al. . |
| 5,389,067 | 2/1995 | Rejai ............... 604/904 |

FOREIGN PATENT DOCUMENTS

| | | |
|---|---|---|
| 2095390 | 11/1993 | Canada . |
| 2153684 | 9/1985 | United Kingdom . |

*Primary Examiner*—John G. Weiss
*Assistant Examiner*—Dennis Ruhl
*Attorney, Agent, or Firm*—Thomas J. Connelly

[57] ABSTRACT

A tampon applicator is disclosed which has a semi-spherically shaped insertion tip for facilitating insertion of a catamenial tampon into a woman's vagina. The tampon applicator includes a first member capable of housing an absorbent tampon. The first member has a central longitudinal axis and first and second ends. An insertion tip is integrally formed on the first end of the first member and extends outwardly therefrom. The insertion tip contains an aperture which extends therethrough and has a side wall which is aligned essentially parallel to the central longitudinal axis. The insertion tip contains a plurality of pleats arranged to form a semi-spherical configuration. The pleats are capable of expanding radially outwardly as the tampon is expelled from the first member. The applicator further includes a second member telescopically mounted in the second end of the first member. The second member is adapted to expel the tampon through the insertion tip as it is pushed into the first member. The tampon applicator is also disclosed in combination with a catamenial tampon.

9 Claims, 2 Drawing Sheets 5,782,793

1

TAMPON APPLICATOR HAVING A SEMI-SPHERICALLY SHAPED PLEATED TIP

This application is a continuation of U.S. Ser. No. 08/422,117 filed Apr. 14, 1995 abandoned, which is a contiuation-in-part of U.S. Ser. No. 08/294,230 filed Aug. 22, 1994, abandoned.

FIELD OF THE INVENTION

This invention relates to a tampon applicator having a semi-spherically shaped pleated tip for facilitating insertion of a catamenial tampon into a body cavity.

BACKGROUND OF THE INVENTION

Catamenial tampons and other types of absorptive media are routinely inserted into body cavities, such as a woman's vagina, to absorb menstrual fluid, blood and other kinds of body fluid. One convenient way to position such absorbent tampons into a body cavity is through the use of an applicator. Comfortable and clean insertion of the absorbent tampon are keys to repeated sale of such applicators. In addition, the applicator should be capable of inserting the absorbent tampon into the body cavity using an acceptable amount of expulsion force.

Tampon applicators are available in a variety of shapes and sizes with the two piece telescopically assembled design being the most prevalent. In the two piece applicator, the tampon is housed in an outer tube and is expelled into a woman's vagina by an inner member which is telescopically mounted in the outer tube and acts as a plunger. Some tampon applicators utilize a hollow tube having an open insertion end through which the tampon is always exposed while other applicators utilize a completely closed or partially closed design. A thin film membrane can cover the insertion end of an applicator to completely enclose the forward end of a tampon while folds and pleats can be used to partially enclose the forward end of a tampon and protect it from contamination. Still other applicators, especially plastic applicators, have a plurality of flexible petals formed on the forward end of the outer tube which can flex radially outward to allow the tampon to be expelled. It will be appreciated that the diameter of the applicator, the material from which it is formed, the basic configuration of the applicator, the size and shape of the tampon positioned in the applicator, as well as the ease of opening the forward end of the applicator will all influence the force required to expel the tampon therefrom. The expulsion force should be kept reasonably low to permit proper functioning of the applicator.

While many have tried to design and manufacture tampon applicators having these improved qualities, there still remains a need for a tampon applicator which is more comfortable to use. Those applicators having an open forward end tend to expose the dry absorbent fibers of the tampon to the interior walls of a woman's vagina and this can cause irritation during insertion. Commercially available plastic applicators, using a plurality of petal tips separated by slots, can sometimes pinch or cut the vaginal tissue of a woman during insertion and cause discomfort. Paper applicators having partially or fully closed tips tend to require an increased expulsion force to expel the tampon from the applicator and this can cause the applicator to deform or cause the tampon to be inserted incorrectly. Such insertion can cause discomfort to the user.

Now a paper tampon applicator has been invented having a semi-spherically shaped pleated tip for facilitating comfortable insertion of an absorbent tampon into a woman's vagina while having a low expulsion force.

SUMMARY OF THE INVENTION

Briefly, this invention relates to a paper tampon applicator having a semi-spherically shaped pleated tip for facilitating insertion of a catamenial tampon into a woman's vagina. The tampon applicator includes a first member capable of housing an absorbent tampon. The first member has a central longitudinal axis and first and second ends. An insertion tip is integrally formed on the first end of the first member and extends outwardly therefrom. The insertion tip contains a small central aperture which extends therethrough and the aperture has a side wall which is aligned essentially parallel to the central longitudinal axis of the first member. The insertion tip contains a plurality of pleats arranged in a semi-spherical configuration. The pleats are capable of expanding radially outward as the tampon is expelled from the first member. The tampon applicator further includes a second member telescopically mounted in the second end of the first member. The second member is adapted to expel the tampon through the insertion tip as it is pushed into the first member.

The tampon applicator is also disclosed in combination with a catamenial tampon having a shaped nose which approximates the interior surface of the first member.

The general object of this invention is to provide a paper tampon applicator having a semi-spherically shaped pleated tip for facilitating insertion of a catamenial tampon into a body cavity. A more specific object of this invention is to provide a tampon applicator having a uniquely formed tip which prevents premature contamination yet substantially encloses the forward end of an absorbent tampon.

Another object of this invention is to provide a tampon applicator having a pleated tip which essentially encloses the forward end of an absorbent tampon and which can be opened with a minimum amount of force.

A further object of this invention is to provide a paper tampon applicator which is economical to manufacture and easy to use.

Still another object of this invention is to provide a paper tampon applicator which will minimize discomfort to a woman when she inserts an absorbent tampon into her vagina.

Still further, an object of this invention is to provide a spirally wound, convolutely wound or longitudinally seamed paper tampon applicator with an improved tip for facilitating insertion of an absorbent tampon into a woman's vagina.

Other objects and advantages of the present invention will become more apparent to those skilled in the art in view of the following description and the accompanying drawings.

DETAILED DESCRIPTION OF THE PREFERRED EMBODIMENTS

Figure 1:
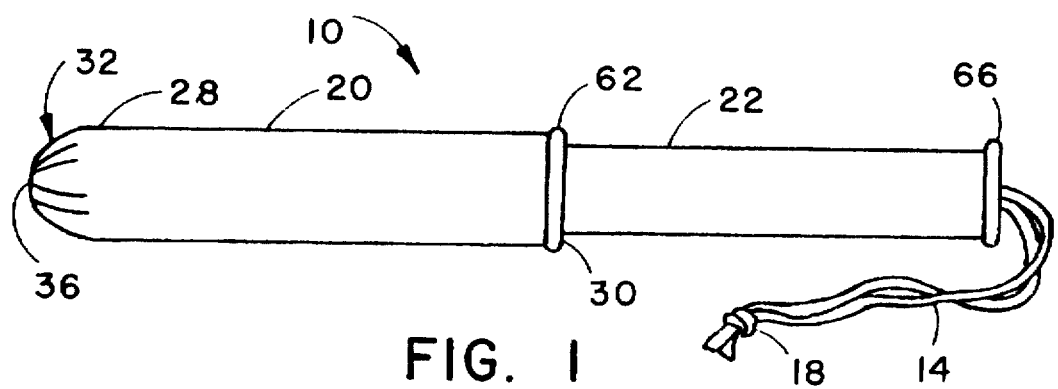
FIG. 1 is a perspective view of a two piece, spirally wound paper tampon applicator.
Figure 2:
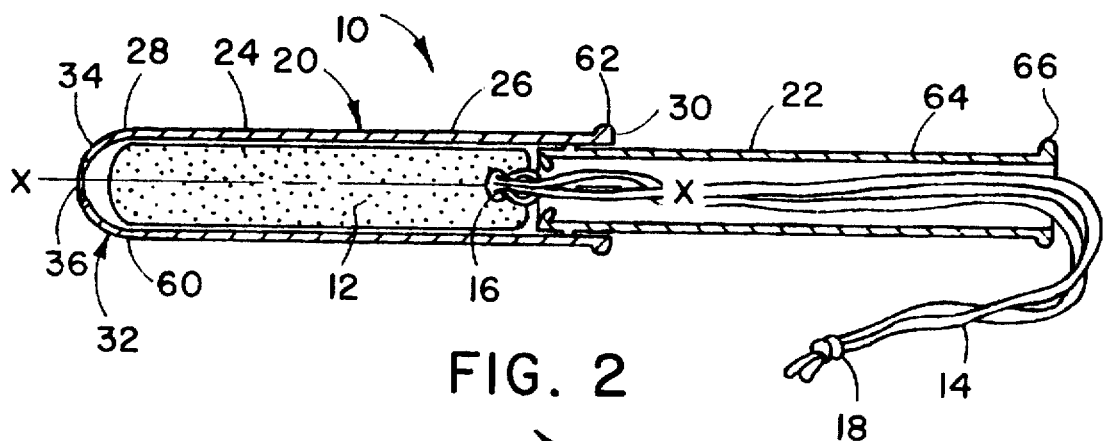
FIG. 2 is a cross-sectional view of the tampon applicator shown in FIG. 1.
Figure 3:
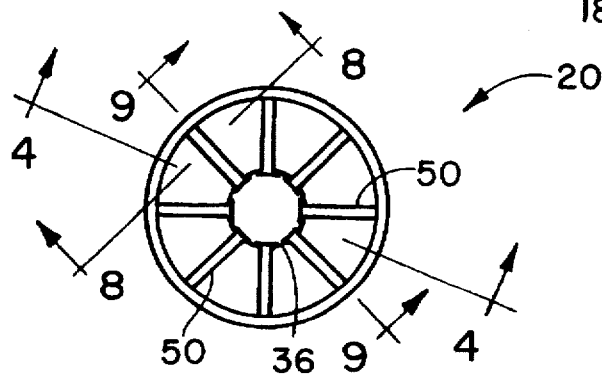
FIG. 3 is a left end view of the tampon applicator shown in FIG. 1 depicting eight pleats.

Referring to FIGS. 1–3, a tampon applicator 10 is shown which is designed to house a catamenial tampon 12 and provide a comfortable means of inserting the tampon 12 into a woman's vagina. A tampon is an absorbent member primarily designed to be worn by a woman during her menstrual period to absorb menses, blood and other body fluid. The tampon 12 can be made from natural or synthetic fibers including cellulose fibers such as cotton or rayon, or artificial fibers such as polyester, polypropylene, nylon or blends thereof. Other types of fibers may also be used, such as cellulose sponge or a sponge formed from elastomeric materials. A blend of cotton and rayon fibers works well.

The tampon 12 is normally compressed into the form of a cylinder and can have a blunt, rounded or shaped forward end. The tampon 12 commonly has a withdrawal string 14 fastened to an end thereof which serves as a means for withdrawing the soiled tampon from the woman's vagina. The withdrawal string 14 can be looped through an aperture 16 formed transversely through the tampon 12. In addition, the withdrawal string 14 can have a knot 18 formed at it's free end to assure that the string 14 will not separate from the tampon 12.

The tampon applicator 10 includes a first member 20 and a second member 22. The first member 20 is preferably in the form of a spirally wound, convolutely wound or longitudinally seamed hollow tube which is formed from paper, paperboard, cardboard or a combination thereof. The first member 20, also commonly referred to as an outer tube, is fairly rigid and has a relatively small diameter of about 10 mm to about 20 mm. The first member 20 has a wall 24 with a predetermined thickness of about 0.2 mm to about 0.6 mm. The wall 24 can be constructed from a single ply of material or be formed from two or more plies which are bonded together to form a laminate. The use of two or more plies or layers is preferred for it enables the manufacture to use certain material in the various layers which can enhance the performance of the tampon applicator 10. When two or more plies are utilized, all the plies can be spirally wound, convolutely wound or longitudinally seamed to form an elongated cylinder. The wall 24 can be constructed using a smooth thin ply of material on the outside or exterior surface 26 which surrounds a coarser and possibly thicker ply. When the wall 24 contains at least three plies, the middle ply can be the thicker ply and the interior and exterior plies can be smooth and/or slippery to facilitate expulsion of the tampon 12 and to facilitate insertion of the first member 20 into a woman's vagina, respectively. By sandwiching a thick, coarser ply of material between two thin, smooth plies, an inexpensive first member 20 can be provided which is very functional. The wall 24 should contain one to four plies, although more plies can be utilized if desired.

The plies forming the wall 24 can be held together by an adhesive, such as glue, or by heat, pressure, ultrasonics, etc. The adhesive can be either water-soluble or water-insoluble. A water-soluble adhesive is preferred for environmental reasons in that the wall 24 will quickly break apart when it is immersed in water. Such immersion will occur should the first member 20 be disposed of by flushing it down a toilet. Exposure of the first member 20 to a municipal's waste treatment plant wherein soaking in water, interaction with chemicals and agitation all occur, will cause the wall 24 to break apart and evenly disperse in a relatively short period of time.

The inside diameter of the first member 20 is usually less than about 0.75 inches (about 19 mm) and preferably less than about 0.625 inches (about 16 mm). Although the exterior diameter of tampons do vary, most tampons utilized by women have an external diameter of less than about 0.75 inches (about 19 mm). However, if one desired to use this invention to administer medication to an animal, such as a farm animal, larger size tampons 12 could be used.

It should be noted that the first member 20 can be spirally wound, convolutely wound or longitudinally seamed into a cylindrical tubular shape. Alternatively, the material can be overlapped into a tubular configuration. Spirally or convolutely winding the first member 20 into a cylindrical tube is especially advantageous when the first member 20 is formed from a laminate. The reason for this is that when a laminate is circumferentially wound into a tube and a butt seam or an overlap is formed, the butt seam or the overlap can interfere with the later formation of pleats on the forward end thereof. A common problem with a rigid or stiff walled, tubular member having a relatively small diameter and a butt seam is that the seam has a tendency to come apart after formation if exposed to certain stress forces and/or high humidity. A problem with a tubular member having an overlap is that a small portion of the wall will be thicker than the remaining portion and this will cause problems when one tries to pleat one end of the tube. Accordingly, the first member 20 should preferably be formed into a cylindrical configuration without the presence of a butt seam or an overlap.

The first member 20 is sized and configured to house the absorbent tampon 12. As stated above, the first member 20 should have a substantially smooth exterior surface 26 which will facilitate insertion of the first member 20 into a woman's vagina. When the exterior surface 26 is smooth and/or slippery, the first member 20 will easily slide into a woman's vagina without subjecting the internal tissues of the vagina to abrasion. The first member 20 can be coated to give it a high slip characteristic. Wax, polyethylene, a combination of wax and polyethylene, cellophane and clay are representative coatings that can be applied to the first member 20 to facilitate comfortable insertion.

The first member 20 can be a straight, elongated cylindrical tube formed on a central longitudinal axis X—X. It is also possible to form the first member 20 into an arcuate shape. The arcuate or curved shape can assist in providing comfort when inserting the first member 20 into a woman's vagina. With a curved tampon applicator, it is possible to employ a curved tampon which again may be more comfortable for some women to use since the shape of the tampon may better fit the curvature of a woman's vagina.

The first member 20 has first and second spaced apart ends 28 and 30, respectively. The first member 20 can also have either a constant outer diameter or a stepped outer profile. Preferably, the first member 20 will have an essentially constant diameter over a major portion of it's length. Integrally formed on the first end 28 of the first member 20 and extending outwardly therefrom is an insertion tip 32. The insertion tip 32 is designed to facilitate insertion of the first member 20 into a woman's vagina in a comfortable manner. The insertion tip 32 is semi-spherical in configuration and has a diameter which is approximately equal to the outside diameter of the first member 20. The insertion tip 32 has a wall 34 with a thickness which is approximately equal to the thickness of the wall 24 which forms the first member 20. However, it is possible to construct the wall 34 so that it has a thickness which is less than or greater than the thickness of the wall 24, if desired.

Figure 4:
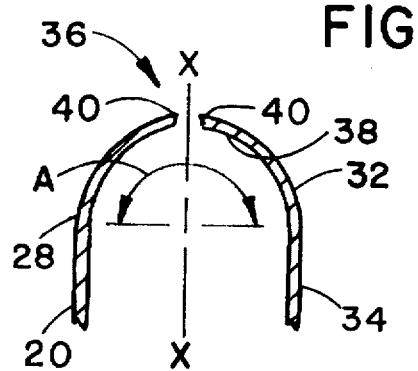
FIG. 4 is a cross-sectional view of the insertion tip taken along line 4—4 of FIG. 3 showing an aperture formed through the insertion tip and the aperture having a side wall aligned essentially parallel to the central longitudinal axis of the first member.

Referring to FIG. 4, the insertion tip 32 is shown in cross-section with the semi-spherical configuration extending outward away from the first end 28 of the first member 20. The cross-section of the semi-spherical configuration spans an arc (A) of approximately 180 degrees. The semi-spherical configuration is formed on a diameter which is sized to be equal to or slightly smaller than the diameter of the first member 20. For example, if the outside diameter of the first member 20 is 0.64 inches (16.2 mm), the insertion tip 32 can be formed on a radius of about 0.32 inches (about 8.1 mm).

A relatively small aperture 36 is formed in the center of the semi-spherical or dome shaped insertion tip 32 and is coaxially aligned with the longitudinal axis X—X. The aperture 36 can have a diameter of at least about 1.5 mm, preferably between about 1.5 to about 5.0 mm, and more preferably, between about 3.0 to about 3.5 mm. Another way of sizing the diameter of the aperture 40 is to make it less than about 30% of the diameter of the first member 20, preferably, between about 10% to about 30% of the diameter of the first member 20, and most preferably, less than about 20% of the diameter of the first member 20. It should be noted that although the aperture 36 is described as a circle, it is possible to form the aperture 36 in other shapes such as a polygon, a square, a pentagon, a hexagon, an octagon, etc. The small aperture 36 should extend through the insertion tip 32 and have a side wall 38 which is aligned essentially parallel to the longitudinal axis X—X. In addition, the aperture 36 can be rounded or contain a radius 40 on it's exterior surface to assure that no sharp edges are present which could pinch or cut the sensitive tissues of a woman's vagina. The purpose of the small aperture 36 in the end of the insertion tip 32 is to facilitate the subsequent unfolding of the pleats during use, as will be described below. The aperture 36 also assures that the pleats will symmetrically open about the longitudinal axis X—X of the first member 20. A further benefit of the aperture 36 is that it provides a visual means for the user to inspect the tampon applicator 10 and assure herself that a tampon 12 is present in the first member 20.

Figure 5:
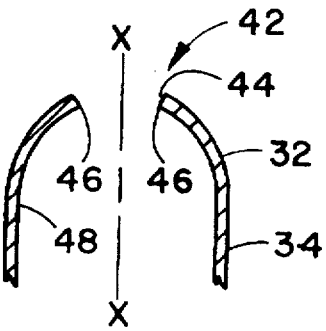
FIG. 5 is a cross-sectional view of an alternative embodiment of an insertion tip integrally formed on the first member and having an aperture formed therethrough wherein the side wall of the aperture is aligned at an angle to the central longitudinal axis of the first member.

The design in FIG. 4 is to be contrasted to the embodiment shown in FIG. 5 wherein an enlarged aperture 42 is depicted having a side wall 44 which tapers downward and inward to form a sharp point 46 adjacent to an interior surface 48 of the insertion tip 32. The sharp point 46 is more likely to pinch or trap vaginal tissue and therefore could cause discomfort during insertion. In addition, the larger diameter of the aperture 42 exposes a greater area of the absorbent tampon 12 and this could cause abrasion with the vaginal tissues during insertion. The embodiment shown in FIG. 4 is more desirable for comfort.

Referring again to FIG. 4, the configuration of the aperture 36 is preferred for it is smaller in diameter and therefore exposes a smaller amount of the absorbent tampon 12. Since a tampon is normally dry and consists of a plurality of absorbent fibers, it can cause abrasion against the walls of a woman's vagina as it is being inserted. By reducing the amount of surface area of the tampon 12 which is exposed to the vaginal tissue, one can decrease the discomfort during the insertion process. In addition, since the insertion tip 32 is almost closed, it also lowers the frictional force between the exterior surface 26 of the tampon applicator 10 and the walls of the vagina. Furthermore, the small diameter of the aperture 36 also decreases the possibility of trapping or pinching vaginal tissue therein.

Figure 6:
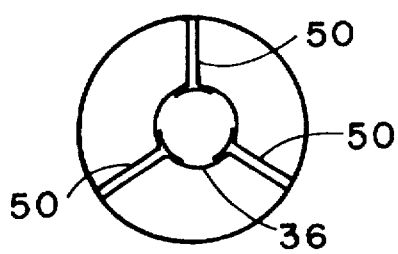
FIG. 6 is an alternative end view of a tampon applicator depicting three pleats.
Figure 7:
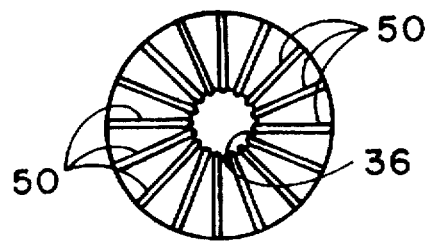
FIG. 7 is still another alternative end view of a tampon applicator depicting sixteen pleats.

Referring to FIGS. 3, 6 and 7, the insertion tip 32 is shown having a plurality of pleats 50 which can radially open such that the insertion tip 32 has a diameter approximately equal to or greater than the diameter of the first member 20. Either an even or an odd number of pleats 50 can be present and the pleats 50 can be equally spaced apart or they can be non-uniformly arranged. Uniformly arranged pleats 50 are preferred but randomly arranged pleats 50 will work. For ease of manufacturing, it is preferred that the pleats 50 be equally spaced relative to one another. Each pleat 50 is a fold formed by doubling the material upon itself and then pressing or adhering the material into place. Although eight equally spaced apart pleats 50 are shown in FIG. 3, it is possible to utilize various numbers of pleats 50. The number of pleats 50 can vary from between three to about thirty-two pleats, preferably between about 5 to about sixteen pleats, and most preferably, between about 6 to about 12 pleats.

In FIG. 6, an embodiment is shown with three equally spaced pleats 50, while in FIG. 7, sixteen pleats 50 are displayed. The minimum number of pleats 50 should be no less than three because the force required to open the insertion tip 32 normally increases as the number of pleats 50 decrease. If the force becomes too large, the tampon applicator 10 could bend or deform during the insertion process and this may cause discomfort. When more than thirty-two pleats 50 are used, the expulsion force may be lowered but it becomes difficult to form so many pleats on the insertion tip 32.

Figure 8:
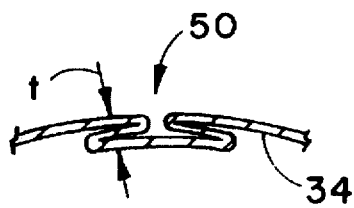
FIG. 8 is a schematic view of a pleat taken along line 8—8 of FIG. 3 depicting the shape and thickness of a pleat.

Referring to FIG. 8, a schematic view of a pleat 50 is shown. The pleat 50 is obtained by folding the paper, paperboard, or cardboard material upon itself so that when each pleat 50 is opened or unfolded it will occupy a much larger surface area. The thickness of the material forming the insertion tip 32 can be equal to or slightly less than the thickness of the first member 20. For the first member 20, a thickness of about 0.1 mm to about 0.7 mm works fine. The insertion tip 32 can have a thickness between about 0.1 mm to about 0.5 mm. In the folded condition, the pleat 50 has a thickness, indicated by the letter "t" of less than about 0.7 mm, preferably between about 0.25 mm to about 0.35 mm. Another way of stating this is to say that the thickness of each pleat 50 in the folded condition will be greater than twice the thickness of the material from which the insertion tip 32 is constructed. One particular apparatus and method for crimping, pleating and forming a tip on a hollow tube is taught in co-pending patent application U.S. Ser. No. 08/300,987 filed Sep. 6, 1994 which is incorporated by reference and made a part hereof.

Figure 9:
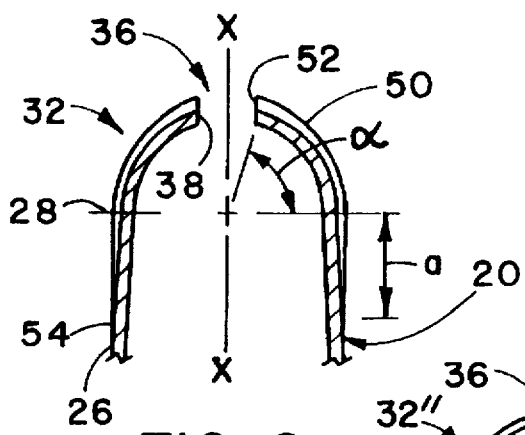
FIG. 9 is a cross-sectional view of the insertion tip taken along line 9—9 of FIG. 3 depicting one end of the pleats extending into the first member.
Figure 10:
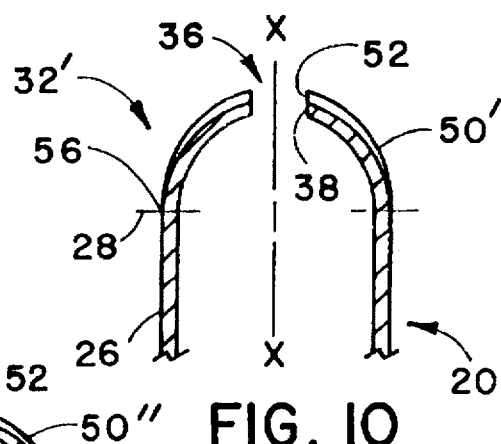
FIG. 10 is a cross-sectional view of an alternative embodiment of the insertion tip showing one end of the pleats terminating at a point where the insertion tip integrally joins the first member.
Figure 11:
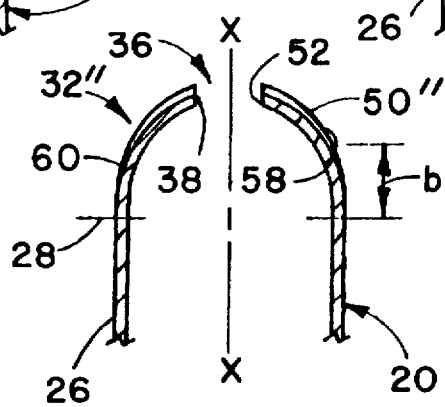
FIG. 11 is a cross-sectional view of another embodiment of the insertion tip showing one end of the pleats terminating at a point on the exterior surface of the insertion tip.

Referring to FIGS. 9–11, three different embodiments of a pleat are depicted. In FIG. 9, the pleat 50 is depicted as having a first end 52 which coincides with the side wall 38 of the aperture 36. In other words, the first end 52 of the pleat 50 forms a portion of the arc of the aperture 36. The pleat 50 also has a second end 54 which coincides with a point located on the exterior surface 26 of the first member 20. This point is spaced a distance "a" from the location where the insertion tip 32 is integrally joined to the first member 20. By forming the pleat 50 with this particular length, one can control the amount of force needed to open the insertion tip 32 and push the tampon 12 therethrough. Usually, a lower force is required to open the pleats when each pleat 50 has a length which extends into the outer circumference of the first member 20.

In FIG. 9, the semi-spherical tip 32 spans a radial arc, identified as angle alpha ($\alpha$), which extends from the first end 52 to the point where the semi-spherical shaped tip 32 is integrally joined to the first member 20. The angle alpha ($\alpha$) is between about 60° to about 90°, preferably between about 75° to about 90°, and most preferably, greater than 80°. The angle alpha ($\alpha$) would be 90° if the aperture 36 was not present. The size of the aperture 36 will partially determine the exact angle of the insertion tip 32. The angle alpha ($\alpha$) should be as close to 90° as possible without completely enclosing the forward end of the tampon 12.

In FIG. 10, an alternative embodiment of an insertion tip 32' is depicted wherein a pleat 50' is shown having a first end 52 which coincides with the side wall 38 of the aperture 36. In other words, the first end 52 of the pleat 50' forms a portion of the arc of the aperture 36. The pleat 50' also has a second end 56 which coincides with the point where the insertion tip 32 is integrally joined to the first end 28 of the first member 20. By forming the pleat 50' with this particular length, one can control the amount of force needed to open the insertion tip 32 and push the tampon 12 therethrough. Although the force required to open the pleats 50' may be slightly greater than the force required with the design shown in FIG. 9, the force is still within acceptable limits.

In FIG. 11, a third embodiment of an insertion tip 32" is depicted wherein a pleat 50" is shown having a first end 52 which coincides with the side wall 38 of the aperture 36. In other words, the first end 52 of the pleat 50" forms a portion of the arc of the aperture 36. The pleat 50" also has a second end 58 which coincides with a point located on an exterior surface 60 of the insertion tip 32. This point is spaced a distance "b" from the location where the insertion tip 32 is integrally joined to the first end 28 of the first member 20. By forming the pleat 50" with this particular length, one can control the amount of force needed to open the insertion tip 32 and push the tampon 12 therethrough. Although the force required to open the pleats 50" may be greater than the force required with the designs shown in FIGS. 9 and 10, the force is still within acceptable limits.

It should be noted that both the length and diameter of commercially available tampons do vary and therefore the tampon applicators 10 should be manufactured in a variety of sizes. Tampons can vary in length from about 1 to about 3 inches (about 25.4 mm to about 76.2 mm) but preferably are about 2 inches (about 50.8 mm) in length. The tampon diameter will also vary from about .25 inches to about 0.75 inches (about 6.4 mm to about 19.0 mm). In addition, the material from which the tampon 12 is constructed, the smoothness of the internal surface of the first member 20, the shape of the second member 22, etc. all contribute to establish a needed expulsion force to open and expel the tampon 12. This force should range from between about 250 grams to about 1,500 grams, preferably less than about 1,200 grams, and most preferably, less than about 1,000 grams. A lower force value is preferred for it assures that the tampon applicator 10 will be less susceptible to being bent or deformed as the tampon 12 is expelled. A bent applicator could cause the tampon to be inserted incorrectly. A lower force value also makes the tampon applicator 10 easier to use.

Referring again to FIGS. 1 and 2, the first member 20 can have a fingergrip ring 62 located approximate the second end 30. The fingergrip ring 62 can be integrally formed from the material from which the first member 20 is constructed or it can be a separate member which is secured in place by an adhesive or some other type of attachment mechanism. The fingergrip ring 62 functions to provide a means for the user to grip the first member 20 and hold it between her thumb and middle finger. The user can then position her forefinger on the free end of the second member 22 and orient the first member 20 relative to her vagina while she pushes the second member 22 into the first member 20.

As stated above, the tampon applicator 10 includes a second member 22, also commonly referred to as an inner tube. The second member 22, like the first member 20, can be a spirally wound, a convolutely wound or a longitudinally seamed hollow tube constructed from paper, paperboard, cardboard, or a combination thereof. The second member 22 can also be formed into a cylindrical tube by overlapping the material upon itself. The second member 22 can be constructed of the same material as the first member 20 or it can be made out of a different material. Furthermore, the second member 22 could be constructed as a laminate having two or more plies which are then spirally wound, convolutely wound or longitudinally seamed into a cylindrical tube. Either a wound tube or a longitudinally seamed tube is preferred because the finished tube will have a wall 64 with a constant thickness. However, some manufacturers may prefer to construct the second member 22 as a solid stick or use some other unique shape. It is also possible to form a fingergrip ring or flange 66 on the outer end of the second member 22 to provide an enlarged surface onto which the user's forefinger can rest. The fingergrip ring 66 thereby functions as a seat for the forefinger and facilitates movement of the second member 22 into the first member 20.

Figure 12:
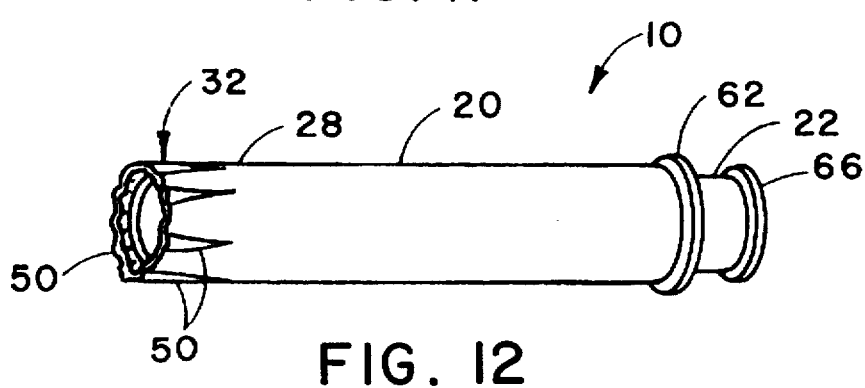
FIG. 12 is a perspective view of the tampon applicator showing the pleats in an open arrangement.

Referring to FIG. 12, the second member 22 functions by being telescopically movable relative to the first member 20. As the second member 22 is pushed into the first member 20, the tampon 12 is forced forward against the pleats 50. The contact by the tampon 12 causes the pleats 50 to radially open to a diameter which is sufficient to allow the tampon 12 to be expelled from the first member 20. The open arrangement of the pleats 50 is shown in FIG. 12 after the tampon 12 has been expelled. With the tampon 12 properly positioned in the woman's vaginal cavity, the tampon applicator 10 is withdrawn and properly discarded.

The tampon applicator 10 having the semi-spherically shaped insertion tip 32 works well in combination with a catamenial tampon having a shaped nose. This is especially true when the shaped nose on the tampon 12 is configured to conform to the interior surface 48 of the insertion tip 32.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A tampon applicator comprising:
   a) a first member capable of housing an absorbent tampon, said first member having a central longitudinal axis and first and second ends;
   b) an insertion tip integrally formed on said first end of said first member and extending outwardly therefrom, said insertion tip having an aperture extending therethrough with a side wall which is aligned essentially parallel to said central longitudinal axis, said insertion tip including a plurality of pleats arranged to form a semi-spherical configuration, said pleats capable of expanding outward as said tampon is expelled from said first member; and
   c) a second member telescopically mounted in said second end of said first member, said second member adapted to expel said tampon through said insertion tip as it is pushed into said first member.

2. A tampon applicator comprising:
   a) a hollow, spirally wound first member capable of housing an absorbent tampon, said first member having a substantially smooth exterior surface, a central longitudinal axis, and first and second ends;
   b) an insertion tip integrally formed on said first end of said first member and extending outwardly therefrom, said insertion tip having an aperture extending therethrough with a side wall which is aligned essentially parallel to said central longitudinal axis, said insertion tip including eight pleats spaced approximately an equal distance apart and arranged to form a semi-spherical configuration, said pleats capable of expanding radially outwardly as said tampon is expelled from said first member; and
   c) a second member telescopically mounted in said second end of said first member, said second member adapted to expel said tampon through said insertion tip as it is pushed into said first member.

3. The tampon applicator of claim 2 wherein said aperture has a diameter of at least about 1.5 mm.

4. The tampon applicator of claim 3 wherein said aperture has a diameter of between about 1.5 mm to about 5.0 mm.

5. The tampon applicator of claim 4 wherein said aperture has a diameter of about 3.0 mm.

6. In combination, a tampon applicator and a catamenial tampon having a shaped nose, said combination comprising:
   a) a catamenial tampon;
   b) a first member capable of housing said catamenial tampon, said first member having a central longitudinal axis and first and second ends;
   c) an insertion tip integrally formed on said first end of said first member and extending outwardly therefrom, said insertion tip having an aperture extending therethrough with a side wall which is aligned essentially parallel to said central longitudinal axis, said insertion tip including a plurality of pleats arranged to form a semi-spherical configuration, said pleats capable of expanding outward as said tampon is expelled from said first member; and
   d) a second member telescopically mounted in said second end of said first member, said second member adapted to expel said catamenial tampon through said insertion tip as it is pushed into said first member.

7. A tampon applicator comprising:
   a) a first member capable of housing an absorbent tampon, said first member being a longitudinally seamed, hollow tube constructed from at least one ply of paper, said tube having a central longitudinal axis, a smooth exterior surface, and first and second ends, said smooth exterior surface being free of any breaks located between said first and second ends;
   b) an insertion tip integrally formed on said first end of said first member and extending outwardly therefrom, said insertion tip having an aperture extending there through with a side wall which is aligned essentially parallel to said central longitudinal axis, said insertion tip including a plurality of pleats arranged to form a semi-spherical configuration, said pleats capable of expanding outward as said tampon is expelled from said first member, and
   c) a second member telescopically mounted in said second end of said first member, said second member adapted to expel an absorbent tampon through said insertion tip as it is pushed into said first member.

8. A tampon applicator comprising:
   a) a hollow first member capable of housing an absorbent tampon, said first member being a longitudinally seamed, hollow tube constructed from at least one ply of paper, said tube having a central longitudinal axis, a substantially smooth exterior surface, and first and second ends, said substantially smooth exterior surface being free of any breaks located between said first and second ends;
   b) an insertion tip integrally formed on said first end of said first member and extending outwardly therefrom, said insertion tip having an aperture extending there through with a side wall which is aligned essentially parallel to said central longitudinal axis, said insertion tip including eight pleats spaced approximately an equal distance apart and arranged to form a semi-spherical configuration, said pleats capable of expanding radially outwardly as said tampon is expelled from said first member, and
   c) a second member telescopically mounted in said second end of said first member, said second member adapted to expel an absorbent tampon through said insertion tip as it is pushed into said first member.

9. In combination, a tampon applicator and a catamenial tampon having a shaped nose, said combination comprising:
   a) a catamenial tampon;
   b) a first member capable of housing said catamenial tampon, said first member being a longitudinally seamed, hollow tube constructed from at least one ply of paper, said tube having a central longitudinal axis, a smooth exterior surface, and first and second ends, said smooth exterior surface being free of any breaks located between said first and second ends;
   c) an insertion tip integrally formed on said first end of said first member and extending outwardly therefrom, said insertion tip having an aperture extending there through with a side wall which is aligned essentially parallel to said central longitudinal axis, said insertion tip including a plurality of pleats arranged to form a semi-spherical configuration, said pleats capable of expanding outward as said tampon is expelled from said first member, and d) a second member telescopically mounted in said second end of said first member, said second member adapted to expel said catamenial tampon through said insertion tip as it is pushed into said first member.

* * * * *